(12) United States Patent
Shieh et al.

(10) Patent No.: US 9,351,941 B2
(45) Date of Patent: May 31, 2016

(54) RADIOFREQUENCY-INDUCED SYNCHRONIZATION OF IN SITU HYPERTHERMIA AND CHEMOTHERAPY VIA MAGNETIC-NANOCONJUGATES

(71) Applicant: National Cheng Kung University, Tainan (TW)

(72) Inventors: Dar-Bin Shieh, Tainan (TW); Chen-Sheng Yeh, Tainan (TW); Tsung-Ju Li, Tainan (TW); Chih-Chia Huang, Tainan (TW)

(73) Assignee: NATIONAL CHENG KUNG UNIVERSITY (TW)

( * ) Notice: Subject to any disclaimer, the term of this patent is extended or adjusted under 35 U.S.C. 154(b) by 57 days.

(21) Appl. No.: 13/905,177

(22) Filed: May 30, 2013

(65) Prior Publication Data

US 2013/0337071 A1    Dec. 19, 2013

Related U.S. Application Data

(60) Provisional application No. 61/652,951, filed on May 30, 2012.

(51) Int. Cl.
| | | |
|---|---|---|
| *A61K 9/16* | (2006.01) | |
| *A61K 9/50* | (2006.01) | |
| *A61K 9/51* | (2006.01) | |
| *A61K 47/48* | (2006.01) | |

(52) U.S. Cl.
CPC ......... *A61K 9/5169* (2013.01); *A61K 47/48569* (2013.01); *A61K 47/48861* (2013.01)

(58) Field of Classification Search
CPC .................. A61K 47/48569; A61K 47/48861; A61K 9/5169
USPC ............................................. 424/178.1, 497
See application file for complete search history.

(56) References Cited

U.S. PATENT DOCUMENTS 8,673,358 B2 * 3/2014 Shieh et al. .................... 424/490
2011/0151586 A1 * 6/2011 Chen et al. ..................... 436/531

FOREIGN PATENT DOCUMENTS

WO    WO2009/093250 A2 *  7/2009  ............. A61K 47/48

OTHER PUBLICATIONS

Wu et al. Nanoscale Res Lett (2008) 3:397-415.*
Wang et al. Macromol. Rapid Commun. 2006, 27, 1665-1669.*

* cited by examiner

*Primary Examiner* — Janet Epps-Smith
(74) *Attorney, Agent, or Firm* — Bacon & Thomas, PLLC

(57) ABSTRACT

The present invention relates to a magnetic nanoparticle for tumor therapy, comprising: a magnetic core; a shell encapsulating a surface of the magnetic core, wherein the shell is made of a polymer with carboxylic groups; a poly-nucleotide chain connected to a surface of the shell; an anti-tumor drug connected to the poly-nucleotide chain, wherein the anti-tumor drug comprises at least one functional group, and each of the functional group is independently a pyrimidine group or a purine group; and an antibody connected to the shell, wherein the antibody identifies a target tumor. In addition, the present invention further provides a method for manufacturing the magnetic nanoparticles for tumor therapy and a pharmaceutical composition containing the magnetic nanoparticles. Accordingly, the magnetic nanoparticle for tumor therapy of the present invention can achieve effective treatment of tumor by synergistic effects between hyperthermia and targeted chemotherapy.

20 Claims, 10 Drawing Sheets

RADIOFREQUENCY-INDUCED SYNCHRONIZATION OF IN SITU HYPERTHERMIA AND CHEMOTHERAPY VIA MAGNETIC-NANOCONJUGATES

CROSS-REFERENCE TO RELATED APPLICATIONS

This nonprovisional application claims priority to U.S. provisional application No. 61/652,951 filed on May 30, 2012.

FIELD OF INVENTION

The present invention relates to a magnetic nanoparticle for tumor therapy, and particularly to a magnetic nanoparticle including an antibody and an anti-tumor drug, which achieves effective treatment of tumor therapy by synergistic effects between hyperthermia and targeted chemotherapy.

DESCRIPTION OF RELATED ART

Nowadays various methods are available for tumor therapy, such as surgical operation, radiation therapy, chemotherapy, hormone therapy, antibody therapy, etc., which are chosen depending on the tumor type, tumor site, severity and health status of the patient.

As for chemotherapy, the bigger challenge lies in the dosage of the chemotherapeutic agent through intravenous delivery. In absence of a target, when the dosage of the chemotherapeutic agent is too low, tumor treatment may be incomplete; however, when the dosage of the chemotherapeutic agent is too high, the patient may be subjected to serious side effects. Accordingly, a target-mediated chemical drug has been developed to overcome the shortcomings of chemotherapy.

In addition, recent studies have discovered the promising potential of magnetic nanoparticles in tumor therapy, wherein part of tumor cells may shrink at a temperature of 41° C.-43° C. The temperature of the magnetic nanoparticles is increased through electromagnetic induction. Accordingly, a number of literatures have recited that the magnetic nanoparticles are used for tumor therapy effectively.

However, although some literatures disclose the combination of magnetic nanoparticles with the target drugs, they do not disclose how to release the combined target drugs through temperature control by taking the advantage of the magnetic nanoparticles. In addition, the literatures fail to disclose how to increase the amount of drug connected to the magnetic nanoparticles, so that the magnetic nanoparticles can carry a sufficient amount of drug for treating tumor.

In view of the above, it will be a blessing for the modern society to benefit from the development of a magnetic nanoparticle capable of effectively combining hyperthermia and targeted chemotherapy, in which treatment of tumor, the main disease of civilization, can be effectively achieved by conducting hyperthermia and targeted chemotherapy simultaneously and synchronously.

SUMMARY OF THE INVENTION

An object of the present invention is to provide a magnetic nanoparticle for tumor therapy, so as to achieve effective treatment of tumor by synergistic effects between drug therapy and hyperthermia through specificity of antibody.

Another object of the present invention is to provide a method for manufacturing a magnetic nanoparticle for tumor therapy, so as to facilitate the combination of anti-tumor drug and the magnetic nanoparticle, and thus when the magnetic nanoparticle is used for hyperthermia treatment through electromagnetic wave, anti-tumor drug release may be increased synchronously.

In order to achieve the above objects, the present invention provides a magnetic nanoparticle for tumor therapy, comprising: a magnetic core; a shell encapsulating a surface of the magnetic core, wherein the shell is made of a polymer with carboxylic groups; a poly-nucleotide chain connected to a surface of the shell; an anti-tumor drug connected to the poly-nucleotide chain, wherein the anti-tumor drug comprises at least one functional group, and each of the functional group is independently a pyrimidine group or a purine group; and an antibody connected to the shell, wherein the antibody identifies a target tumor.

The magnetic core is a material at least selected from the group consisting of: Fe, $Fe_3O_4$, $Fe_2O_3$, Pt, Ni, Au, $SiO_2$, and a combination thereof. Preferably, the magnetic core is a material at least selected from a group consisting of: Fe, $Fe_3O_4$, $Fe_2O_3$, Pt, Au, and a combination thereof. More preferably, the magnetic core is a material at least selected from a group consisting of: $Fe_3O_4$, Pt, Au, and a combination thereof. The magnetic core of the present invention can be made of a single metal, a metal compound, an alloy including more than one metal, or a nanoparticle having a core-shell structure. For example, the magnetic core can be a magnetic core of iron-platinum alloy (FePt), a magnetic core of iron core-gold shell (Fe@Au), or a magnetic core of iron oxide core-silica shell ($Fe_3O_4$@$SiO_2$). Furthermore, the magnetic core of the present invention has an average particle diameter of 5 to 100 nm, preferably 10 to 50 nm, and more preferably 20 to 40 nm.

In the magnetic nanoparticle for tumor therapy of the present invention, the material of the shell layer may be poly(acrylic acid) (PAA), poly(styrene-alt-maleic acid) (PSMA), or a combination thereof, and preferably poly(styrene-alt-maleic acid) (PSMA).

In addition, in the present invention, the nucleotide type and the chain length of the multi-nucleotide chain are not particularly limited. The nucleotide may be adenine (A), guanine (G), cytosine (C), thymine (T), uracil (U), or a combination thereof; and the nucleotide chain length may be between 5 to 20 nucleotides. In the present invention, the multi-nucleotide chain is preferably a poly-adenine (poly-A) consisting of 10 to 15 adenine (A).

Furthermore, in the present invention, the anti-tumor drug is pyrimidine antagonist, or purine antagonist. The anti-tumor drug is preferably pyrimidine antagonist such as 5-fluorouracil (5-FU), arabinosylcytosine, capecitabine, gemcitabine, or a combination thereof, and more preferably 5-fluorouracil (5-Fu), among which, 5-Fu is a common pyrimidine antagonist as an anti-tumor drug, which can be complementarily combined with adenine in the DNA of the target tumor to block DNA synthesis of the target tumor thereby achieving achieves effective treatment of tumor therapy.

In the magnetic nanoparticle of the present invention, the antibody connected to the shell is an antibody for tumor identification, whose goal is to increase the combination probability of the magnetic nanoparticle of the present invention with target tumor. Herein, suitable tumors to be treated by the present invention are not particularly limited, and the present invention can be used to treat different tumors by choosing appropriate antibody and anti-tumor drug accordingly. Treatment on bladder cancer and oral cancer are particularly preferred.

In the magnetic nanoparticle for tumor therapy of the present invention, the antibody may be connected to the shell through a hydrophilic polymer chain. In the above, the polymer chain may be an amine-PEG, or chitin/chitosan having amine on its two ends, wherein the amine on one end is used for connecting the carboxylic group of the shell, the amine on the other end is used for connecting antibody.

The magnetic nanoparticle for tumor therapy of the present invention significantly increases the efficacy of tumor therapy by synergistic effects between hyperthermia and targeted chemotherapy. The magnetic field frequency used for inducing the temperature raise of the magnetic nanoparticle may be between 300 kHz to 220 MHz, or between 100 kHz to 8 MHz. In the present invention, the magnetic field frequency is preferably 1.3 MHz. In addition, when the magnetic nanoparticle is heated to between 40° C. to 50° C. through the magnetic field frequency, the release rate of the anti-tumor drug on the magnetic nanoparticle may reach between 80% to 100%. Accordingly, the magnetic nanoparticle of the present invention cannot only achieve hyperthermia treatment through heating of magnetic field, but also drug treatment through synchronous releasing of the anti-tumor drug during the heating.

The present invention also provides a method for manufacturing a magnetic nanoparticle for tumor therapy, comprising: providing a magnetic core; forming a shell encapsulating a surface of the magnetic core, wherein the shell is made of a polymer with carboxylic groups; forming at least one poly-nucleotide chain on the shell; forming at least one anti-tumor drug on the poly-nucleotide chain, wherein the anti-tumor drug comprises at least one functional group, and each the functional group is independently a pyrimidine group or a purine group; and forming at least one antibody on the shell, wherein the antibody identifies a target tumor.

In the above method, the polynucleotide chain may be formed on the shell in a solution including dimethylformide (DMF). Preferably, the polynucleotide chain is formed on the shell in a solution including dimethylformide (DMF) with 1-ethyl-3-(3-dimentylaminopropyl)carbodiimide hydrochloride/N-hydroxysuccinimide (EDC/NHS). As a result, at least 900 polynucleotide chains may be formed on the shell of each of the magnetic nanoparticle of the present invention. In comparison to the EDC/NHS solution, the EDC/NHS DMS solution may advantageously increase the amount of the polynucleotide chains formed on the shell.

In the method of the present invention, the limitations on the material of the magnetic core, the particle diameter of the magnetic core, the material of the shell, and the condition of the polynucleotide chain, as well as selection of anti-tumor drug, and the characteristic that the anti-tumor drug may be formed on the shell through a polynucleotide chain, are the same as those for the magnetic nanoparticle for tumor therapy of the present invention, therefore further description will not be repeated here.

Furthermore, the present invention also provides a pharmaceutical composition for tumor therapy, comprising: a magnetic nanoparticle for tumor therapy and a pharmaceutical acceptable carrier. The magnetic nanoparticle for tumor therapy is the same as the magnetic nanoparticle for tumor therapy of present invention, and it comprises: a magnetic core, a shell encapsulating a surface of the magnetic core, wherein the shell is made of a polymer with carboxylic groups; a poly-nucleotide chain connected to a surface of the shell; an anti-tumor drug connected to the poly-nucleotide chain, wherein the anti-tumor drug comprises at least one functional group, and each of the functional group is independently a pyrimidine group or a purine group; and an antibody connected to the shell, wherein the antibody identifies a target tumor; and a pharmaceutical acceptable carrier.

In the pharmaceutical composition of the present invention, features such as the material of the magnetic core, the particle diameter of the magnetic core, the material of the shell, and the condition of the polynucleotide chain, as well as selection of anti-tumor drug, and the formation of the anti-tumor drug on the shell through a polynucleotide chain, are the same as those for the magnetic nanoparticle for tumor therapy of the present invention, and therefore further description will not be repeated here. However, as for the pharmaceutical acceptable carrier, it can be one selected from the group consisting of active agents, adjuvants, dispersing agents, wetting agents, and suspending agents. Examples of the pharmaceutical acceptable carrier include physiological saline, phosphate buffer, polyethylene glycol, methyl cellulose, a hydrophilc colloid, etc.

In addition, in an embodiment according to the present invention, targeting hyperthermia and chemotherapy through tail vein injection of the 5-FU-loaded $Fe_3O_4$@anti-HER2 nanoparticle (500 µg/mL) in a serial single daily dose for four consecutive days are evaluated. RF treatments are given 24 h after the nanoparticle had been injected. Compared with the PBS control group, there is significant tumor regression in the $Fe_3O_4$-anti-HER2+5-FU/RF exposure group (FIG. 8) that finally led to complete remission of the disease in all test animals in the group. 5-FU injection alone (770 nM, equivalent to total nanoparticle loaded drugs) is unable to suppress tumor growth. The absence of RF induced hyperthermia treatment without 5-FU release also fails to stop tumor proliferation. Thermo Tracer H2640 (NEC, Japan) camera records the increase in tumor temperature above 42° C. after 15 min in 5-FU-loaded $Fe_3O_4$@anti-HER2 nanoparticle treatment, but PBS treatment did not. This indicates nanoparticle accumulation within tumor dissipate sufficient heat to generate hyperthermia effect. A pathological examination again showed massive autolysis of tumor cells compared with PBS-treatment control and a decrease in tumor size in $Fe_3O_4$-anti-HER2+5-FU/RF exposure group In summary, the magnetic nanoparticle for tumor therapy of the present invention may facilitate the combination of anti-tumor antibody with the target tumor and be induced for heating by the electromagnetic wave. As a result, the magnetic nanoparticles can perform hyperthermia treatment while releasing the anti-tumor drugs at the same time, thereby achieving synchronization of hyperthermia and drug therapy, which significantly improves the effect of tumor treatment.

LIST OF REFERENCE NUMERALS

1 Magnetic core
2 Shell
3 Polynucleotide chain
4 Anti-tumor drug
5 Polymer chain
6 Antibody

DETAILED DESCRIPTION OF THE PREFERRED EMBODIMENT

Hereafter, examples will be provided to illustrate the embodiments of the present invention. Other advantages and effects of the invention will become more apparent from the disclosure of the present invention. Other various aspects also may be practiced or applied in the invention, and various modifications and variations can be made without departing from the spirit of the invention based on various concepts and applications.

Embodiment 1 —Preparation of Magnetic Nanoparticle for Tumor Therapy

Figure 1:
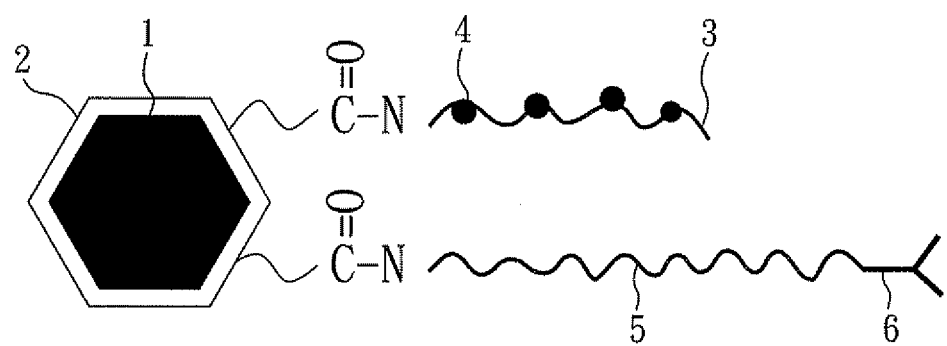
FIG. 1 is a schematic diagram of the magnetic nanoparticle for tumor therapy of the embodiment 1 according to the present invention.

In reference to FIG. 1, the figure shows the magnetic nanoparticle for tumor therapy of the embodiment 1 according to the present invention, the magnetic core 1 is a $Fe_3O_4$ exterior layer of an octahedron; the shell 2 is PSMA, wherein the PSMA has multiple carboxylic groups; then, polynucleotide chain 3 poly-$A_{15}$ is formed on the carboxylic groups of the shell 2; multiple anti-tumor drugs 4,5-Fu are formed on the polynucleotide chains 3; furthermore, PEG polymer chain 5 having amine on its two ends is further formed on the carboxylic group, and an antibody 6 may be formed on the other amine end, so that the magnetic nanoparticle of the present embodiment have the property of tumor targeting.

Figure 2A:
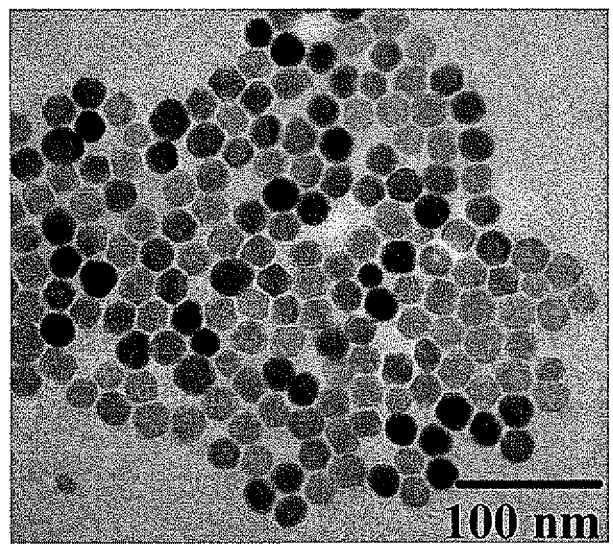
FIG. 2A shows a TEM picture of the $Fe_3O_4$@PSMA magnetic nanoparticle of the embodiment 1 according to the present invention.
Figure 2B:
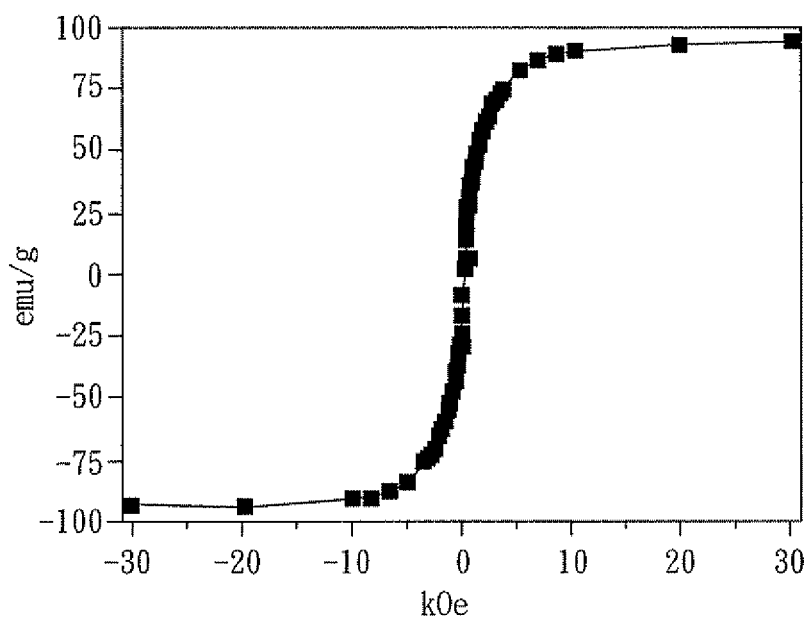
FIG. 2B shows the result of the saturation magnetic susceptibility for the $Fe_3O_4$@PSMA magnetic nanoparticle of the embodiment 1 according to the present invention.

For preparing the magnetic nanoparticles, the first step is, to perform pyrolysis on the solution containing Fe(acac)3, oleic acid, and trioctylamine at 350° C. for 30 minutes, to form a $Fe_3O_4$ magnetic nanoparticle covered with oleic acid. Since the $Fe_3O_4$ magnetic nanoparticle covered with oleic acid is hydrophobic, effort to make the $Fe_3O_4$ magnetic nanoparticle hydrophilic requires, in the present embodiment, modifying the surface of $Fe_3O_4$ magnetic nanoparticle with PSMA, since PSMA is a polymer having multiple carboxylic groups and able to effectively attach to the surface of the $Fe_3O_4$ magnetic nanoparticle. Therefore, through the hydrophilic property of the PSMA carboxylic group, replacing the oleic acid covering the $Fe_3O_4$ magnetic nanoparticle can form hydrophilic $Fe_3O_4$ magnetic nanoparticle (represented here as: $Fe_3O_4$@PSMA). FIG. 2A is a TEM picture of the $Fe_3O_4$@PSMA magnetic nanoparticle of the embodiment 1 according to the present invention. As shown in FIG. 2A, appearance of the $Fe_3O_4$@PSMA is an octahedral structure having a particle diameter of 22 nm. Then, as shown in FIG. 2B, which shows the result of the saturation magnetic susceptibility for the $Fe_3O_4$@PSMA magnetic nanoparticle of the embodiment 1 according to the present invention, under 300K, the saturation magnetic susceptibility of $Fe_3O_4$@PSMA is 94 emu/g, accordingly, $Fe_3O_4$@PSMA thus has excellent magnetization characteristics.

In the present invention, the anti-tumor drug is 5-Fu, since the core structure of 5-Fu is similar to the structure of the uracil, which can be combined with adenine through a hydrogen bond, in the present embodiment, poly-adenine (poly-A) needs to be formed on a surface of the $Fe_3O_4$@PSMA in order to form a magnetic nanoparticle having multiple adenine chains (represented here by: $Fe_3O_4$@PSMA-poly-$A_{15}$), so as to connect 5-Fu to $Fe_3O_4$@PSMA-poly-$A_{15}$ to form $Fe_3O_4$@PSMA-poly-$A_{15}$/5-Fu. Also, since Her-2 proteins highly expresses in many kinds of tumor cells, Her-2 antibody is appropriate to be applied in tumor targeting. $Fe_3O_4$@PSMA and Her-2 antibody are connected through the PEG having amines on its two ends (amine-PEG) according to the present invention, to form the Her-2 antibody on the $Fe_3O_4$@PSMA magnetic nanoparticle (represented here as: $Fe_3O_4$@PSMA poly-$A_{15}$/5-Fu@anti-Her2 or represented here as $Fe_3O_4$@anti-Her2).

Figure 3A:
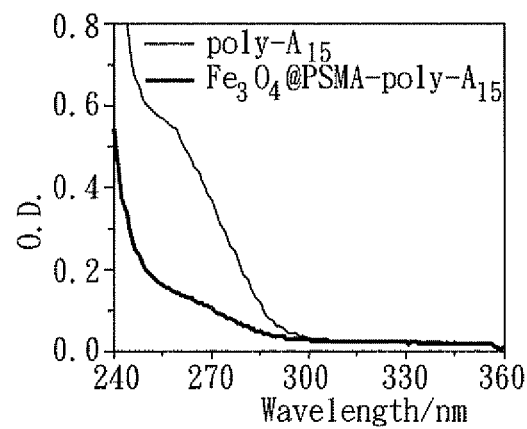
FIG. 3A shows the result from a measurement for poly-$A_{15}$ of the embodiment 1 according to the present invention.
Figure 3B:
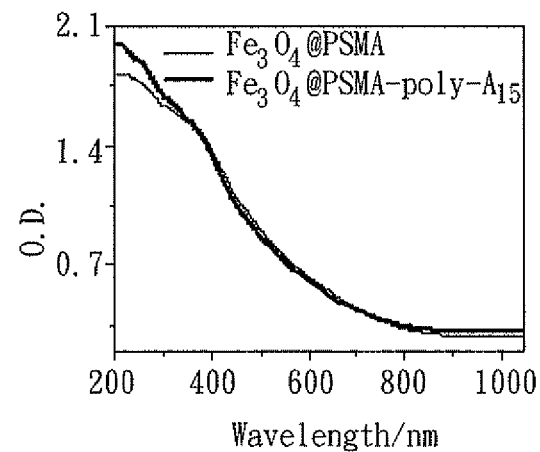
FIG. 3B shows another result from a measurement for poly-$A_{15}$ of the embodiment 1 according to the present invention.
Figure 3C:
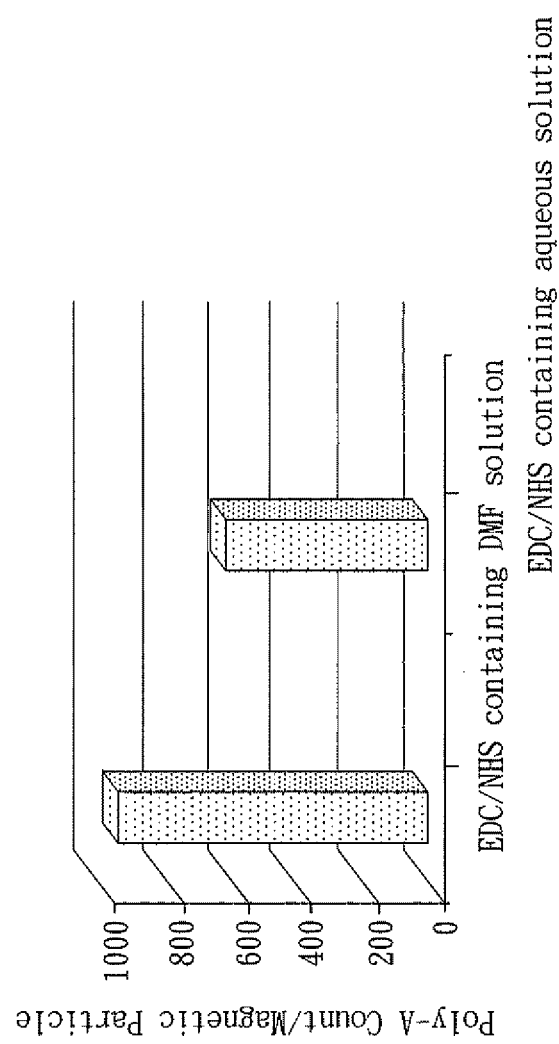
FIG. 3C shows the result of connection efficiency for poly-$A_{15}$ of the embodiment 1 according to the present invention.

In preparing $Fe_3O_4$@PSMA poly-$A_{15}$, according to the present embodiment, 0.06 ml, 3.6 μM of poly-$A_{15}$ with an aminated 5' end are added into 1 ml of $Fe_3O_4$@PSMA magnetic nanoparticle solution (280 ppm), wherein, the solution is a DMS solution containing EDC/NHS. FIG. 3A shows the result from a measurement for poly-$A_{15}$ of the embodiment 1 according to the present invention, wherein, when poly-$A_{15}$ with an aminated 5' end is detected at a wavelength of 260 nm, in comparison to the curve for poly-$A_{15}$ with an aminated 5' end, the apparently lowed curve for $Fe_3O_4$@PSMA-poly-$A_{15}$ shows that poly-$A_{15}$ is successfully connected to $Fe_3O_4$@PSMA. Also, as shown in FIG. 3B, which is another result from a measurement for poly-$A_{15}$ of the embodiment 1 according to the present invention, a wavelength of about 260 nm is used for detecting, and it also testifies that poly-$A_{15}$ is successfully connected to $Fe_3O_4$@PSMA to form a structure of $Fe_3O_4$@PSMA-poly-$A_{15}$. Then, as shown in FIG. 3C which shows the result of connection efficiency for poly-$A_{15}$ of the embodiment 1 according to the present invention, in the DMS solution containing EDC/NHS, each $Fe_3O_4$@PSMA magnetic nanoparticle has approximately 950 strands of poly-$A_{15}$, however in the aqueous solution containing EDC/NHS, each $Fe_3O_4$@PSMA magnetic nanoparticle has only about 624 strands of poly-$A_{15}$, thereby proving that under the condition of DMF solution containing EDC/NHS, poly-$A_{15}$ has the best connection efficiency. Then, after $Fe_3O_4$@PSMA-poly-$A_{15}$ is completed, 50 μM of 5-Fu antitumor drug is added and mixed homogenously at 4° C. for 24 hours, so as to form 5-Fu on $Fe_3O_4$@PSMA-poly-$A_{15}$ (represented here as: $Fe_3O_4$@PSMA-poly-$A_{15}$/5-Fu). 5-Fu carriage of each $Fe_3O_4$@PSMA-poly-$A_{15}$/5-Fu is detected at a wavelength of 266 nm. Additionally, results of zeta potential measurement can also show that after $Fe_3O_4$@PSMA-poly-$A_{15}$ is combined with 5-Fu, the zeta potential changes from −10 mV to −20 mV. The result here proves that 5-Fu is successfully formed on $Fe_3O_4$@PSMA-poly-$A_{15}$.

Figure 4A:
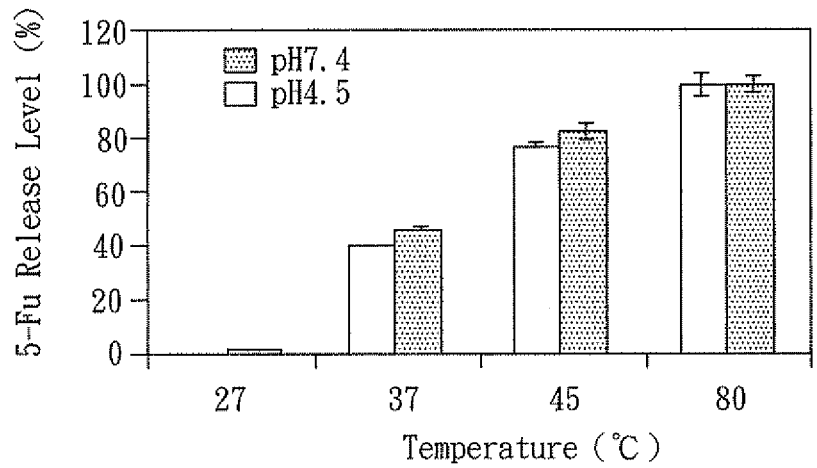
FIG. 4A shows the result of temperature mediated release of 5-Fu of the embodiment 1 according to the present invention.
Figure 4B:
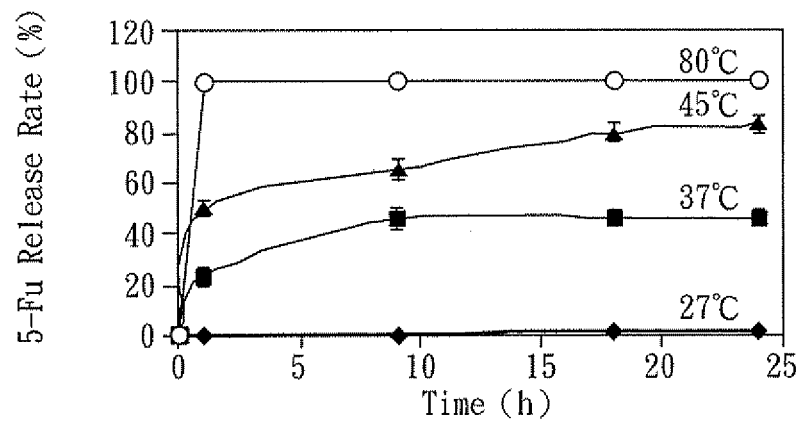
FIG. 4B shows the result of temperature mediated release of 5-Fu at pH 7.4 of the embodiment 1 according to the present invention.
Figure 4C:
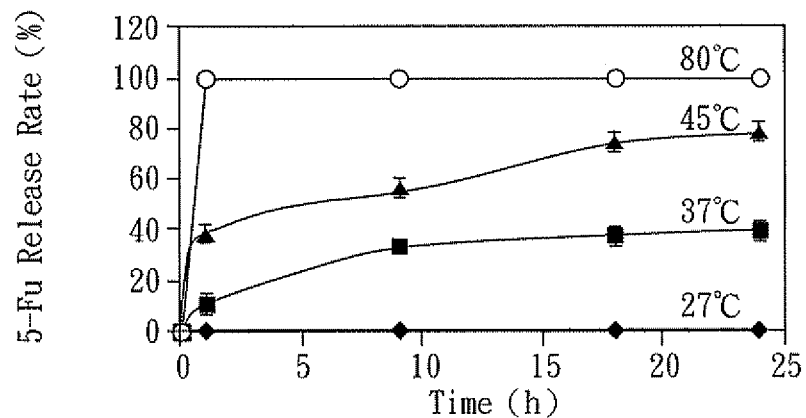
FIG. 4C shows the result of temperature mediated release of 5-Fu at pH 4.5 of the embodiment 1 according to the present invention.

Since the 5-Fu formed on $Fe_3O_4$@PSMA-poly-$A_{15}$ in the present embodiment has the property of temperature mediated release, therefore, a wavelength of 266 nm is used to detect and confirm the property of temperature mediated release. $Fe_3O_4$@PSMA-poly-$A_{15}$/5-Fu is detected at temperatures of 27° C., 37° C., 45° C., 80° C., and respectively for pH 7.4 and pH 4.5, for 24 hours. FIG. 4A shows the result of temperature mediated release of 5-Fu of the embodiment 1 according to the present invention. First, 5-Fu is independent from effect of pH value, and, experimental findings at 45° C. for 24 hours reveals that 5-Fu release rate almost reaches between 80% to 100%; particularly at 80° C., 5-Fu release rate can even reach 100%. In addition, FIG. 4B and FIG. 4C also show that at 80° C., 5-Fu can be 100% released in 1 hour; at 45° C., 5-Fu is gradually released in more amount as time progresses. It will then be understood that when $Fe_3O_4$@PSMA-poly-$A_{15}$/5-Fu magnetic nanoparticle is heated to 40° C. to 50° C. by an electromagnetic wave, the release rate of 5-Fu can reach as high as 80% to 100%.

Furthermore, in order to increase the tumor targeting property of the $Fe_3O_4$@PSMA-poly-$A_{15}$/5-Fu magnetic nanoparticle according to the present embodiment, PEG having amines on its two ends (amine-PEG) is further formed on the $Fe_3O_4$@PSMA surface, wherein, amine group on one end of the amine-PEG is connected to the carboxylic group on a surface of the $Fe_3O_4$@PSMA, while the other end is connected to Her-2 monoclonal antibody, to form $Fe_3O_4$@PSMA-poly-$A_{15}$/5-Fu magnetic nanoparticle connected with Her-2 monoclonal antibody (represented here by: $Fe_3O_4$@PSMA-poly-$A_{15}$/5-Fu@anti-Her2).

Embodiment 2 —Tumor Therapy Efficacy Determination for $Fe_3O_4$@anti-Her2 In-Vitro $Fe_3O_4$@PSMA-poly-$A_{15}$/5-Fu@anti-Her2 magnetic nanoparticle will be abbreviated into $Fe_3O_4$@anti-Her2 magnetic nanoparticle in the present embodiment.

Figure 5A:
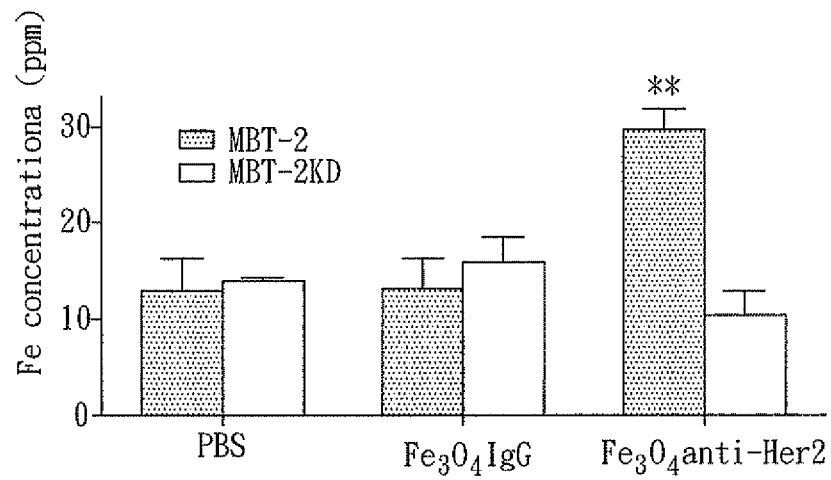
FIG. 5A shows the result of the tumor targeting efficacy of $Fe_3O_4$@anti-Her2 magnetic nanoparticle of the embodiment 2 according to the present invention.
Figure 5B:
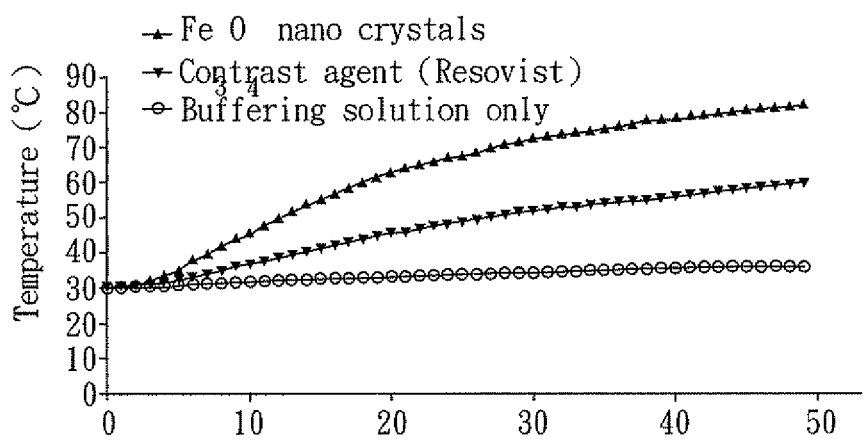
FIG. 5B shows the temperature variation of $Fe_3O_4$@anti-Her2 magnetic nanoparticle induced by electromagnetic wave of the embodiment 2 according to the present invention.

In order to demonstrate that the $Fe_3O_4$@anti-Her2 magnetic nanoparticle of the present embodiment has the effect for tumor targeting, $Fe_3O_4$@anti-Her2 magnetic nanoparticle of experimental group and Fe3O4@IgG magnetic nanoparticle of control group are employed to conduct the experiments on mouse bladder cancer cell lines MBT-2 highly expressing Her-2 and mouse bladder cancer cell lines MBT-2KD with 12% reduced expression level of Her-2. Next step is to detect the combination of $Fe_3O_4$@anti-Her2 magnetic nanoparticle with the tumor cell lines through measuring the iron content of the tumor cell lines. The result of such is shown in FIG. 5A, FIG. 5A shows the result of the tumor targeting efficacy of $Fe_3O_4$@anti-Her2 magnetic nanoparticle of the embodiment 2 according to the present invention. In the MBT-2 cell lines, the amount of $Fe_3O_4$@anti-Her2 combined in the MBT-2 cell lines is significantly larger than PBS group and $Fe_3O_4$@IgG control group, as such, it can be seen that the $Fe_3O_4$@anti-Her2 of the present embodiment indeed has superior tumor targeting effect. Because $Fe_3O_4$@anti-Her2 has a high magnetic susceptibility, it can be heated by electromagnetic wave induction. As shown in FIG. 5B showing the temperature variation of $Fe_3O_4$@anti-Her2 magnetic nanoparticle induced by electromagnetic wave of the embodiment 2 according to the present invention, under the influence of 1.3 MHz electromagnetic wave induction, juxtaposed against a contrast agent and a buffer solution, temperature of $Fe_3O_4$@anti-Her2 gradually increases with the time progressing, wherein, the temperature can already reach 40° C. to 50° C. after 10 seconds, 80° C. after 50 seconds, because of $Fe_3O_4$@anti-Her2 of the present embodiment which is confirmed to indeed be heated through electromagnetic wave induction.

Figure 5C:
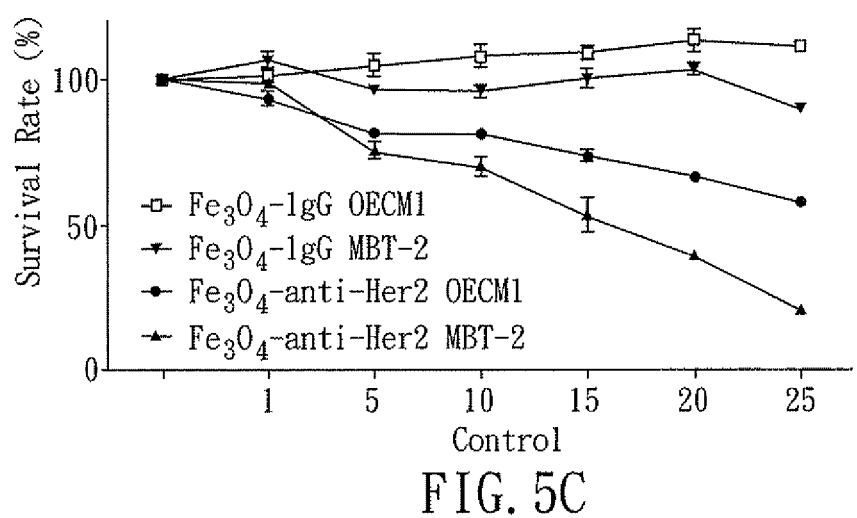
FIG. 5C shows the result of tumor cells surviving resistance of $Fe_3O_4$@anti-Her2.

Next, for the purpose of further confirming the therapeutic effect of $Fe_3O_4$@anti-Her2 against tumor cells, the present embodiment puts bladder cancer cell lines MBT-2 and oral cancer cell lines OEC-M1 under test. The MBT-2 cell lines and OEC-M1 cell lines are cultured in a 96 well plate to reach a the cell density of $5\times10^3$ cells/well, wherein, the culturing condition for the MBT-2 cell line is: under the condition of 0.5% $CO_2$ at 37° C., the cell line is cultured in a DMEM culture medium with 10% FBS and 1% composite antibiotics (antibiotic/antimycotic, GIBCO); the culturing condition for OEC-M1 cell line is: the cell line is cultured in a PRMI-1640 culture medium having 10% FBS and 1% composite antibiotics (antibiotic/antimycotic, GIBCO) under 0.5% $CO_2$ at 37° C. After 12 hours of culturing, $Fe_3O_4$@anti-Her2 magnetic nanoparticles (experimental group) and $Fe_3O_4$@IgG (control group) are added respectively to a final concentration of 50 μg/ml, and after further culturing for 12 hours to make the magnetic nanoparticle and the tumor cell lines to be fully combined, tumor cells were washed with PBS buffer solution to get rid of extra $Fe_3O_4$@anti-Her2 and $Fe_3O_4$@IgG magnetic nanoparticles. React with a wire ring having a field intensity of 32 Kvar for 5 minutes to induce $Fe_3O_4$@anti-Her2 and $Fe_3O_4$@IgG to heat, and then after 24 hours, a cell viability test (MTT assay) is performed at a wavelength of 595 nm. The result of such is shown in FIG. 5C which shows the result of tumor cells survival of $Fe_3O_4$@anti-Her2. For the MBT-2 cell lines and OEC-M1 cell lines, under the condition of addition of $Fe_3O_4$@anti-Her2, the viability of the two are significantly lowered. As for the control experiment of $Fe_3O_4$@IgG, cell viability substantially remains constant. Therefore, the $Fe_3O_4$@anti-Her2 magnetic nanoparticle of the present embodiment can indeed effectively restrain the growth of tumor cells relying on its characteristic of the tumor targeting.

Embodiment 3 Tumor Therapy Efficacy Determination for $Fe_3O_4$@anti-Her2 In-Vivo Two groups of 6-8 months old C3H/HeN male mice transplanted with MBT2 cell lines are prepared, one of which is male mice with MBT2 tumor having a tumor volume smaller than 50 $mm^3$ (the small tumor) and the other is male mice with a MBT2 tumor having a tumor volume larger than 50 $mm^3$ (the large tumor).

Figure 6A:
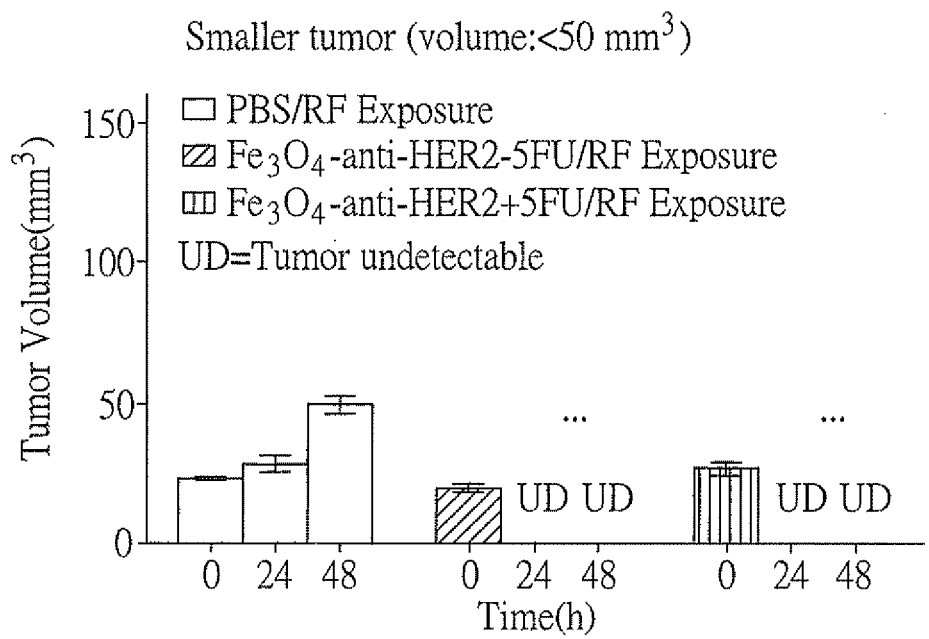
FIG. 6A shows the result for small tumor therapy by $Fe_3O_4$@anti-Her2 magnetic nanoparticles of the embodiment 3 according to the present invention.

At first, the therapeutic efficacy of $Fe_3O_4$@anti-Her2 magnetic nanoparticle for the small tumor therapy is tested. The experiment is divided into Groups 1-4, wherein PBS is directly injected into the small tumors in Group 1, Group 2; 100 μg/ml of $Fe_3O_4$@anti-Her2 magnetic nanoparticles without 5-Fu is injected into the small tumor in Group 3; and 100 μg/ml of $Fe_3O_4$@anti-Her2 magnetic nanoparticles with 5-Fu is directly injected into the small tumor in Group 4. Next, the tumor of Groups 2-4 is exposed to a 1.3 MHz electromagnetic wave for 15 minutes, followed by respectively measuring the tumor sizes in Groups 1-4 using a caliper, and the result is shown in FIG. 6A, which shows the result for small tumor therapy by $Fe_3O_4$@anti-Her2 magnetic nanoparticles of the embodiment 3 according to the present invention. It can be seen from Group 1 and Group 2 that the size of the MBT2 tumor is not under control, but appears to grow gradually; however, in Group 3 and Group 4, after 24 hours and 48 hours, the MBT2 tumor size approaches near 0 mm³. As a result, with respect to a small tumor of less than 50 mm³, it can be understood that an early treatment based on electromagnetic wave induced hyperthermia or its combination with drug therapy can effectively suppress tumor growth and achieve the effect on tumor therapy.

Figure 6B:
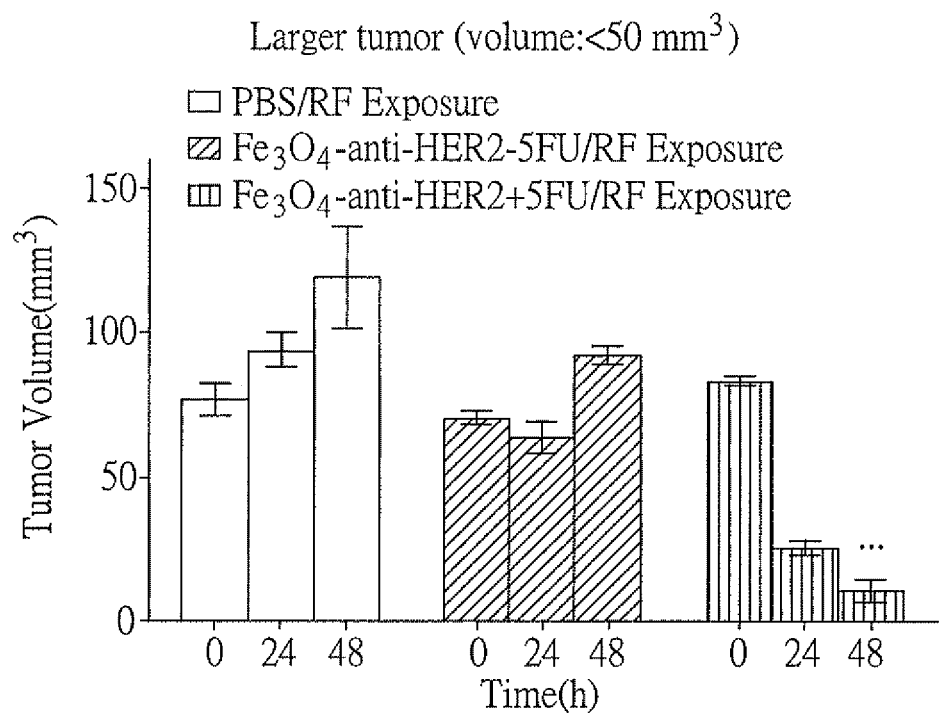
FIG. 6B shows the result for large tumor therapy by $Fe_3O_4$@anti-Her2 magnetic nanoparticles of the embodiment 3 according to the present invention.

Then, examination for the therapeutic effect of $Fe_3O_4$@anti-Her2 on the male mice with the MBT2 tumor having a tumor volume larger than a 50 mm³ is performed. This examination is divided into Groups 1-4, wherein Group 1 to Group 4 respectively involves injecting directly 100 μg/ml of PBS, contrast agent, $Fe_3O_4$@anti-Her2 without 5-Fu, and $Fe_3O_4$@anti-Her2 with 5-Fu into the respective tumors, and then, exposing the tumors of Groups 1-4 to a 1.3 MHz electromagnetic wave for 15 minutes, and lastly measuring the tumor size using a caliper, the result of which is shown in FIG. 6B, demonstrating the treatment of the $Fe_3O_4$@anti-Her2 magnetic nanoparticle against large tumor. In Group 1 and Group 2, after 24 hours and 48 hours, tumor size of the MBT2 tumor does not appear to be suppressed but rather shows sign of increased growth; while in Group 3, after 48 hours, tumor size of the MBT2 tumor appears to increase; however, in Group 4, after 48 hours, tumor size of the MBT2 tumor apparently shrinks, and the magnitude of such is close to 2 folds. It can therefore be understood from this result that, $Fe_3O_4$@anti-Her2 magnetic nanoparticle with 5-Fu can not only work well in small tumor therapy, but also considerably well in large tumor therapy.

It will be understood from the above findings that, the $Fe_3O_4$@anti-Her2 magnetic nanoparticle of the present invention can effectively suppress tumor growth and achieve the effect on tumor therapy due to the combination of hyperthermia with target drug therapy.

Figure 7:
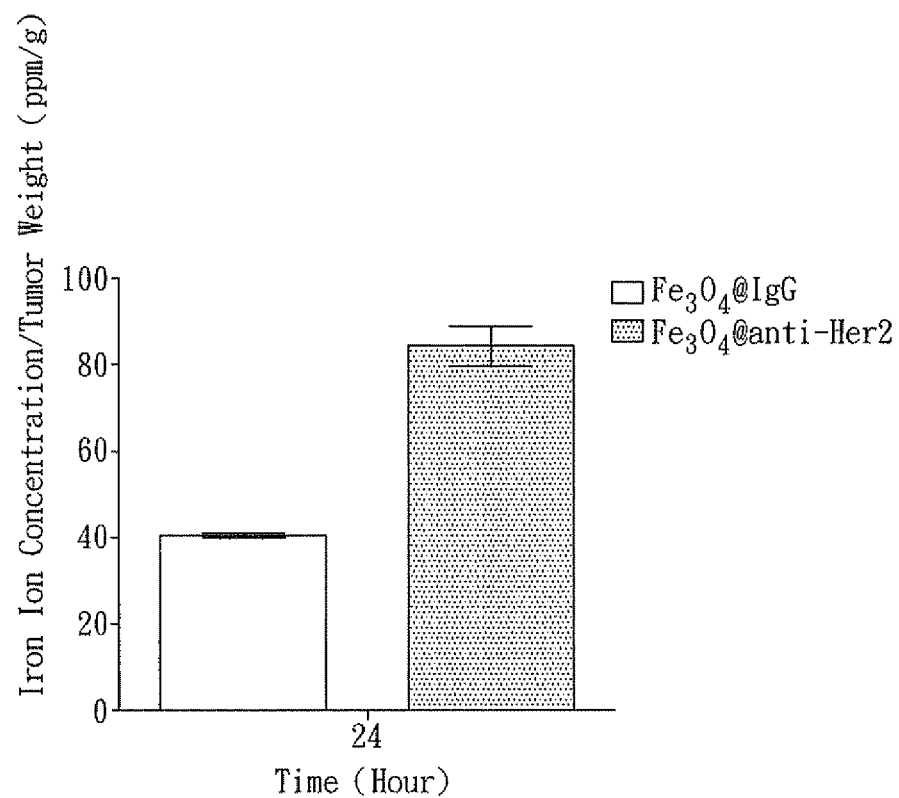
FIG. 7 shows the result of the tumor targeting efficacy of $Fe_3O_4$@anti-Her2 magnetic nanoparticle of the embodiment 3 according to the present invention.

However, in part of patients suffering from tumor metastasis, the tumor cell may be transferred to other tissues via the circulatory system. In order to confirm that the $Fe_3O_4$@anti-Her2 magnetic nanoparticle of the present embodiment can work for target therapy against specific tumor cells through the circulatory system, therefore through tail vein injection, 100 μg/ml of $Fe_3O_4$@anti-Her2 magnetic nanoparticle is injected into a male mouse bearing with MBT2 tumor cell. The result as shown in FIG7 which shows the result of the tumor targeting efficacy of $Fe_3O_4$@anti-Her2 magnetic nanoparticle of the embodiment 3 according to the present invention, wherein $Fe_3O_4$@IgG magnetic nanoparticle is the control group while $Fe_3O_4$@anti-Her2 magnetic nanoparticle is the experimental group, and through measuring the iron (Fe) content in the tumor cell, the amount of magnetic nanoparticle targeting on the tumor can be determined. It can be seen from the results of FIG. 7 that through tail vein injection, $Fe_3O_4$@anti-Her2 magnetic nanoparticle can achieve the effect of targeting through the circulatory system.

Embodiment 4 — Organ [Fe] Distribution Evaluation In-Vivo

Groups of male $C_3H$/HeN mice 6-8 weeks old in this experiment were given a tail-vein injection of 200 μL 5-FU-loaded $Fe_3O_4$@anti-HER2 magnetic nanoparticle in PBS (500 m/mL iron) or of PBS alone. One group of mice was sacrificed 24 h after the tail-vein injection. The rest of the mice were given 15 min RF treatment 24 h after the tail-vein injection. Twenty-four hours after the RF treatment, the mice were overdosed with the anesthetics ketamine and xylazine (8.7 mg/100 g and 1.3 mg/100 g), and their major organs (brain, heart, lungs, spleen, liver, kidneys) and blood were collected. Each organ was homogenized and dissolved in nitro-hydrochloric acid. The sample solutions were continuously shaken for two days to ensure Fe dissociation. All samples were filtered before analyzed using atomic absorption spectrometer (Solar M6 series; Unicam, UK).

And then, thermogram analysis is performed using the injection method described in the previous paragraph, 5-FU-loaded $Fe_3O_4$@anti-HER2 nanoparticle or PBS was given to 6-8 week old male $C_3H$/HeN mice. A camera (Thermo Tracer H2640; NEC, Tokyo, Japan) was fixed vertically 60 cm above the anesthetized mice. Thermal data were recorded in real-time at 640×480 pixels, and temperature images were analyzed with thermal analysis simulation (TAS) software.

Figure 8:
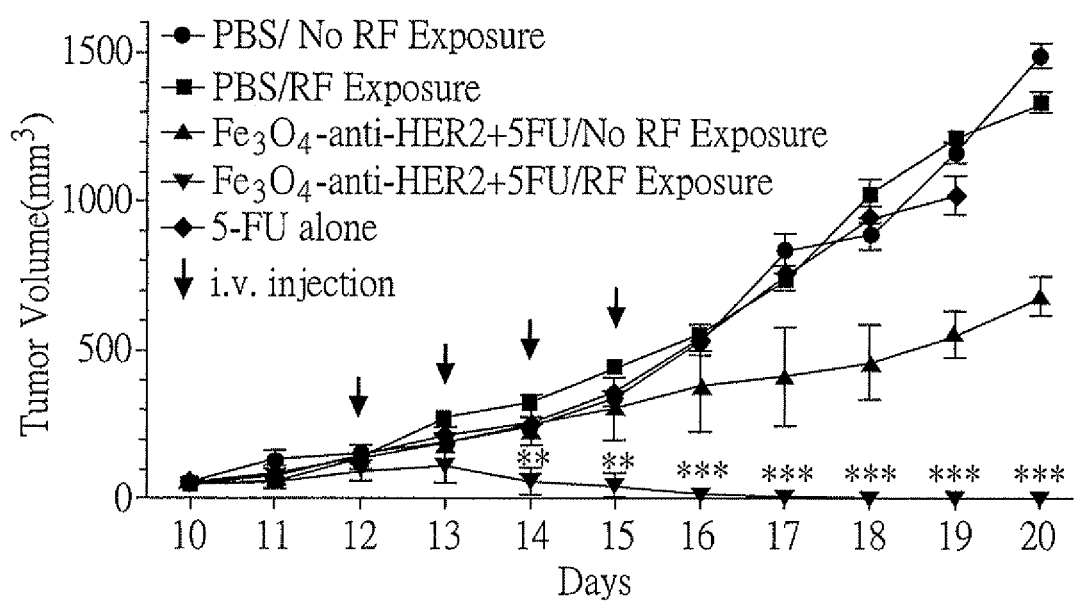
FIG. 8 shows the result of RF treatment which was done 24 h after the nanoparticle had been injected, wherein the 5-FU-loaded $Fe_3O_4$@anti-HER2 nanoparticle (500 μg/mL) group mice (n=4) were intravenously injected through the tail vein one dose per day for 4 days.

The result of Embodiment 4 is shown in FIG. 8, wherein the 5-FU-loaded $Fe_3O_4$@anti-HER2 nanoparticle (500 μg/mL) group mice (n=4) were intravenously injected through the tail vein one dose per day for 4 days. RF treatment was done 24 h after the nanoparticle had been injected. Compared with the PBS control group (n=4), there was significant post-treatment tumor regression in the nanoparticle group subjected to 1.3 MHz RF treatment. A histopathology examination of the cancer tissue was done after $4^{th}$ dose. The PBS control group showed intact cancer cells. Similar pathological results were observed in comparison with PBS treatment and decrease in tumor size after local RF induced hyperthermia treatment.

In the above embodiments it is proven that, first, the $Fe_3O_4$@anti-Her2 magnetic nanoparticle of the present invention, prepared by a specific preparation method, can not only achieve to an effective combination of hyperthermia with target drug therapy, but also achieve the largest anti-tumor drug carriage, as a result, such design can effectively enhance the therapeutic efficacy of the magnetic nanoparticle of the present invention against tumor cells; furthermore, the results of in-vitro and in-vivo experiments can prove that the $Fe_3O_4$@anti-Her2 magnetic nanoparticle of the present invention does not only exhibit excellent characteristic of tumor targeting, but also can combine hyperthermia with drug therapy, so that through performing hyperthermia and releasing the anti-tumor drug at the same time, the tumors that cannot be treated by hyperthermia can be further eradicated by drug therapy. In addition, from tissue analysis result, it can be observed that tumor tissues treated by $Fe_3O_4$@anti-Her2 magnetic nanoparticle may be subjected to effusion of red blood cells and tissue necrosis because of damaged blood capillaries adjacent thereto. Consequently, the Fe3O4@anti-Her2 magnetic nanoparticle of the present invention can be effective in tumor therapy by simultaneously indeed performing hyperthermia and drug target therapy.

The above embodiments are only for the purpose of better describing the present invention and are of exemplary nature, the scope of right asserted by the present invention is based on the scope of claims in this application, and are not intended to be limited by the above embodiments.

What is claimed is:

1. A magnetic nanoparticle for tumor therapy, comprising:
   a magnetic core;
   a shell fully encapsulating a surface of the magnetic core, wherein the shell is made of a polymer with carboxylic groups;
   a poly-nucleotide chain connected to a surface of the shell, wherein the poly-nucleotide chain is a poly-adenine chain with an aminated end, and the poly-adenine chain connects to the surface of the shell via the aminated end of the poly-adenine chain;
   an anti-tumor drug connected to the poly-nucleotide chain, wherein the anti-tumor drug comprises at least one functional group, and each of the functional group is independently a pyrimidine group or a purine group; and an antibody connected to the shell through a hydrophilic polymer chain, wherein the antibody identifies a target tumor, and the hydrophilic polymer chain contains amines on its two ends, wherein the amine on one end connects the carboxylic groups of the shell, and the amine on the other end connects the antibody;

wherein the anti-tumor drug is employed to perform tumor growth inhibition or modulation of tumor microenvironment, and wherein a local radio frequency is provided for inducing hyperthermia during the treatment of the magnetic nanoparticle for tumor therapy, and wherein the induced hyperthermia will synchronize the triggered release of anti-tumor modalities and thereby enhance the therapeutic efficacy through synergistic activity.

2. The magnetic nanoparticle of claim 1, wherein the magnetic core is made of a material selected from the group consisting of Fe, $Fe_3O_4$, $Fe_2O_3$, Pt, Ni, and a combination thereof.

3. The magnetic nanoparticle of claim 1, wherein the magnetic core has an average particle diameter of 5-100 nm.

4. The magnetic nanoparticle of claim 1, wherein the shell is made of poly(acrylic acid), poly(styrene-alt-maleic acid), or a combination thereof.

5. The magnetic nanoparticle of claim 1, wherein the shell is made of poly(styrene-alt-maleic acid).

6. The magnetic nanoparticle of claim 1, wherein the anti-tumor drug is 5-fluorouracil, arabinosylcytosine, capecitabine, gemcitabine, or a combination thereof.

7. The magnetic nanoparticle of claim 1, wherein the anti-tumor drug is 5-fluorouracil.

8. The magnetic nanoparticle of claim 1, wherein the anti-tumor drug has a release rate of 80-100% at 40-50° C.

9. A method for manufacturing a magnetic nanoparticle for tumor therapy, comprising the steps of:

providing a magnetic core;

forming a shell fully encapsulating a surface of the magnetic core, wherein the shell is made of a polymer with carboxylic groups;

forming at least one poly-nucleotide chain on the shell, wherein the poly-nucleotide chain is formed on the shell in a solution comprising dimethylformide (DMF), and the poly-nucleotide chain is a poly-adenine chain with an aminated end;

forming at least one anti-tumor drug on the poly-nucleotide chain, wherein the anti-tumor drug comprises at least one functional group, and each of the functional group is independently a pyrimidine group or a purine group; and forming at least one antibody on the shell through a hydrophilic polymer chain, wherein the antibody identifies a target tumor, and the hydrophilic polymer chain contains amines on its two ends, wherein the amine on one end connects the carboxylic groups of the shell, and the amine on the other end connects the antibody;

wherein the anti-tumor drug is employed to perform tumor growth inhibition or modulation of tumor microenvironment, and wherein a local radio frequency is provided for inducing hyperthermia during the treatment of the magnetic nanoparticle for tumor therapy, wherein the induced hyperthermia will synchronize the triggered release of anti-tumor modalities and thereby enhance the therapeutic efficacy through synergistic activity.

10. The method of claim 9, wherein the magnetic core is made of a material selected from the group consisting of Fe, $Fe_3O_4$, $Fe_2O_3$, Pt, Ni, or a combination thereof.

11. The method of claim 9, wherein the magnetic core has an average particle diameter of 5-100 nm.

12. The method of claim 9, wherein the shell is made of poly(acrylic acid), poly(styrene-alt-maleic acid), or a combination thereof.

13. The method of claim 9, wherein the anti-tumor drug is 5-fluorouracil, arabinosylcytosine, capecitabine, gemcitabine, or a combination thereof.

14. A pharmaceutical composition for tumor therapy, comprising:

an effective amount of a magnetic nanoparticle for tumor therapy, which comprises:

a magnetic core;

a shell fully encapsulating a surface of the magnetic core, wherein the shell is made of a polymer with carboxylic groups;

a poly-nucleotide chain connected to a surface of the shell, wherein the poly-nucleotide chain is a poly-adenine chain with an aminated end, and the poly-adenine chain connects to the surface of the shell via the aminated end of the poly-adenine chain;

an anti-tumor drug connected to the poly-nucleotide chain, wherein the anti-tumor drug comprises at least one functional group, and each of the functional group is independently a pyrimidine group or a purine group; and an antibody connected to the shell through a hydrophilic polymer chain, wherein the antibody identifies a target tumor, and the hydrophilic polymer chain contains amines on its two ends, wherein the amine on one end connects the carboxylic groups of the shell, and the amine on the other end connects the antibody; and a pharmaceutical acceptable carrier;

wherein the anti-tumor drug is employed to perform tumor growth inhibition or modulation of tumor microenvironment, and wherein a local radio frequency is provided for inducing hyperthermia during the treatment of the magnetic nanoparticle for tumor therapy wherein the induced hyperthermia will synchronize the triggered release of anti-tumor modalities and thereby enhance the therapeutic efficacy through synergistic activity.

15. The pharmaceutical composition of claim 14, wherein the pharmaceutically acceptable carrier is at least one selected from a group consisting of:

active agents, adjuvant agents, dispersion agents, wetting agents, and suspension agents.

16. The pharmaceutical composition of claim 14, wherein the magnetic core is made of a material selected from the group consisting of Fe, $Fe_3O_4$, $Fe_2O_3$, Pt, Ni, or a combination thereof.

17. The pharmaceutical composition of claim 14, wherein the magnetic core has an average particle diameter of 5~100 nm.

18. The pharmaceutical composition of claim 14, wherein the shell is made of poly(acrylic acid), poly(styrene-alt-maleic acid), or a combination thereof.

19. The pharmaceutical composition of claim 14, wherein the anti-tumor drug is 5-fluorouracil, arabinosylcytosine, capecitabine, gemcitabine, or a combination thereof.

20. The magnetic nanoparticle of claim 1, wherein the magnetic core is $Fe_3O_4$; the anti-tumor drug is 5-fluorouracil; and the antibody is anti-Her2.

* * * * *